United States Patent
Kim et al.

(10) Patent No.: US 8,513,402 B2
(45) Date of Patent: *Aug. 20, 2013

(54) HUMAN SERUM ALBUMIN-SIRNA NANO-SIZED CARRIER SYSTEM

(75) Inventors: Kwangmeyung Kim, Seoul (KR); Ick Chan Kwon, Seoul (KR); Kuiwon Choi, Seoul (KR); In Chan Youn, Seoul (KR); MyungSook Huh, Seoul (KR); Sojin Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 16 days.

This patent is subject to a terminal disclaimer.

(21) Appl. No.: 13/245,180

(22) Filed: Sep. 26, 2011

(65) Prior Publication Data

US 2012/0083455 A1    Apr. 5, 2012

(30) Foreign Application Priority Data

Oct. 5, 2010 (KR) .................. 10-2010-0097038

(51) Int. Cl.
*C07H 21/04*    (2006.01)

(52) U.S. Cl.
USPC ........................................ 536/24.5

(58) Field of Classification Search
USPC ........................................ 536/24.5
See application file for complete search history.

(56) References Cited

U.S. PATENT DOCUMENTS

| | | | |
|---|---|---|---|
| 8,257,733 B2 * | 9/2012 | Desai et al. .............. 424/450 |
| 2003/0166512 A1 * | 9/2003 | Xie .............................. 514/7 |
| 2005/0225636 A1 | 10/2005 | Maemura et al. | |
| 2006/0178297 A1 | 8/2006 | Troy et al. | |
| 2006/0275371 A1 * | 12/2006 | Dai et al. ................... 424/489 |
| 2008/0039412 A1 * | 2/2008 | Jadhav et al. ............... 514/44 |
| 2010/0113695 A1 | 5/2010 | Papineni et al. | |
| 2011/0159098 A1 | 6/2011 | Slager | |

FOREIGN PATENT DOCUMENTS

| | | |
|---|---|---|
| CN | 1515244 | 7/2004 |
| CN | 1646702 A | 7/2005 |
| CN | 101001615 | 7/2007 |
| CN | 101500937 | 8/2009 |
| CN | 101501058 | 8/2009 |
| JP | 2005-276056 | 10/2005 |
| JP | 2010-74362 | 4/2010 |
| WO | WO03/069306 A2 | 8/2003 |
| WO | 2009/082817 | 7/2009 |

OTHER PUBLICATIONS

Abbasi et al. Cell Biochem. Biophys. 2011, 61:277-287.*
Daniela Reischl et al., "Drug delivery of siRNA therapeutics: potentials and limits of nanosystems", Nanomedicine: Nanotechnology, Biology, and Medicine, vol. 5, 2009, pp. 8-20.
Saghir Akhtar et al., "Nonviral delivery of synthetic siRNA in vivo", The Journal of Clinical Investigation, vol. 117, No. 12, Dec. 2007, pp. 3623-3632.
Yifeng Shi et al., "Research advances in improving the pharmacokinetics of protein drugs by utilizing human serum albumin as a carrier", Chin Med Biotechnol, vol. 3, No. 6, Dec. 2008, pp. 454-456.
Chinese Office Action issued Aug. 28, 2012 in corresponding Chinese Patent Application No. 201110309352.1.
Chinese Office Action mailed Apr. 28, 2013 for corresponding Chinese Application No. 201110309352.1.

* cited by examiner

*Primary Examiner* — Brian Whiteman
(74) *Attorney, Agent, or Firm* — Staas & Halsey LLP

(57) ABSTRACT

Disclosed are a human serum albumin-siRNA carrier system having siRNA bound to human serum albumin and a user thereof, and especially, human serum albumin-siRNA carrier system, which has a biodegradable covalent bond between human serum albumin polymer and siRNA and is stable in a living body, and a user thereof.
The human serum albumin-siRNA carrier system having the biodegradable covalent bond between the human serum albumin and the siRNA exhibits high siRNA delivery efficiency to a target site in the living body. Therefore, the human serum albumin-siRNA carrier system may allow siRNA for therapy to be efficiently delivered to a target site such as cancer tissues in the living body even by being administrated in a relatively low concentration, which may result in a wide use for therapies of various diseases.

9 Claims, 5 Drawing Sheets
(3 of 5 Drawing Sheet(s) Filed in Color)

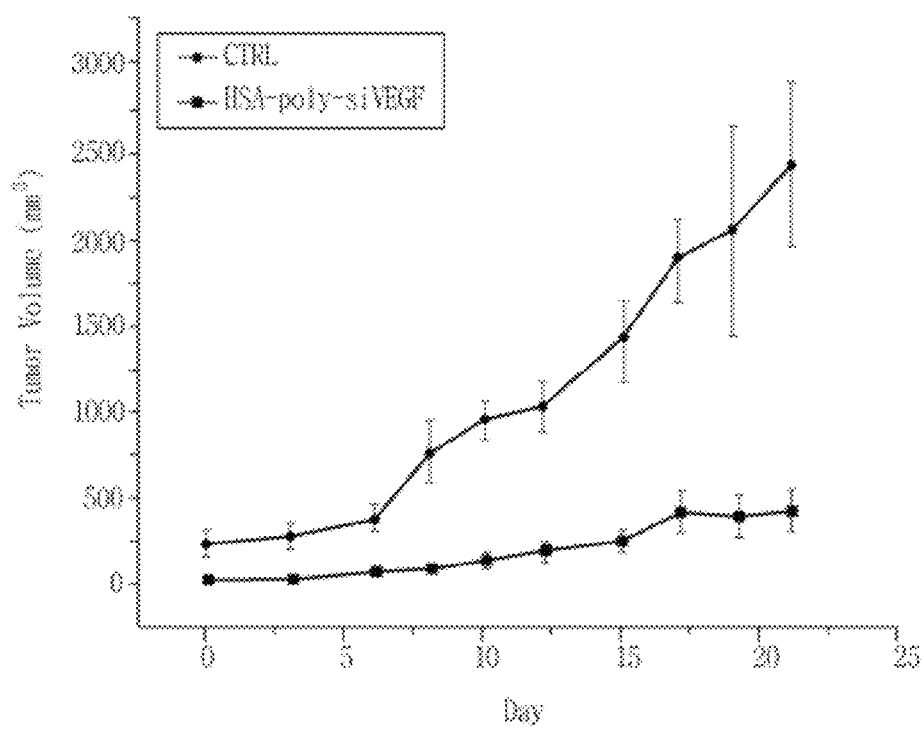

HUMAN SERUM ALBUMIN-SIRNA NANO-SIZED CARRIER SYSTEM

CROSS-REFERENCE TO RELATED APPLICATION

Pursuant to 35 U.S.C. §119(a), this application claims the benefit of earlier filing date and right of priority to Korean Application No. 10-2010-0097038, filed on Oct. 5, 2010, the contents of which is incorporated by reference herein in its entirety.

BACKGROUND OF THE INVENTION

1. Field of the Invention

This specification relates to a human serum albumin-siRNA carrier system that siRNA is bound to the human serum albumin and a use thereof, and more particularly, to a human serum albumin-siRNA nano-sized carrier system, which is prepared by binding the human serum albumin and siRNA and has an enhanced in vivo stability, and a use thereof.

2. Background of the Invention

Gene therapies are classified into a method of recovering a damaged function by making a specific gene carried (delivered) to or expressed in a cell when a specific protein is not expressed in the corresponding cell due to gene loss or gene variation, and a method for recovering a normal function by selectively inhibiting over-expression of proteins causing diseases or over-expression of unnecessary proteins by a gene delivery such as siRNA. Such control of protein expression at the gene level is to approach the cause of disease, so it is being regarded as an ideal treatment.

The key to the gene therapy using siRNA relies on how to deliver siRNA having strong negative charges to a desired tissue with minimize side effects and exhibit efficiencies. However, siRNA has a low cell permeability, and is easily degraded without maintaining a necessary concentration due to being sensitive to breakdown enzymes of genes under physiological circumstance and the like, which causes several limitations to use of the siRNA as drugs.

To overcome such problems, it is required to develop gene carrier systems, which can help siRNA to be effectively circulated without removed or discharged by the immune cells in a living body or the like, to be stably delivered/accumulated on a specific disease sites, and to be appropriately biodegraded. As one of in vivo polymer substances, serum albumin is a type of protein, which is very biocompatible and also very stable as having 19-day half-life within blood. The serum albumin is well-known as having high affinity and effective cancer accumulation ability, and thus appropriate to be used as a gene carrier system.

SUMMARY OF THE INVENTION

Therefore, to overcome the above mentioned problems, an aspect of the detailed description is to provide a novel siRNA carrier system capable of enhancing in vivo stability and delivery efficiency of siRNA, and a pharmacologic composition containing the siRNA carrier system.

To achieve the aspect in accordance with the purpose of this specification, as embodied and broadly described herein, there is provided a human serum albumin-siRNA carrier system, employing a binding (bonding, bond), capable of existing in form of nano-sized particles in an aqueous system by virtue of formation of complex with siRNA and being lysed from siRNA in a specific physiological circumstance, for increasing a delivery efficiency in a living body.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

EFFECT OF THE INVENTION siRNA carrier system according to the detailed description is a stable nano-sized siRNA carrier system, which is prepared by modifying human serum albumin to be bound to siRNA by a biodegradable covalent bond, thereby allowing siRNA to be stably delivered to a target site in a living body. Therefore, the siRNA carrier system can be applied to not only various cancers but also other disease models, which may result in effective use in future for extensive disease treatments.

BRIEF DESCRIPTION OF THE DRAWINGS

The application file contains at least one drawing executed in color. Copies of this patent application publication with color drawinq(s) will be provided by the Office upon request and payment of the necessary fee. The accompanying drawings, which are included to provide a further understanding of the invention and are incorporated in and constitute a part of this specification, illustrate exemplary embodiments and together with the description serve to explain the principles of the invention.

In the drawings:

FIG. 6 is a mouse tumor growth curve that is inhibited by VEGF poly-siRNA delivery when T-HSA/poly-siRNA complexes are fabricated using poly-siRNA for cancer growth factor VEGF by a method of Example 2 to be administrated in a mouse, into which human prostatic carcinoma cell lines are grafted.

DETAILED DESCRIPTION OF THE INVENTION

Figure 1:
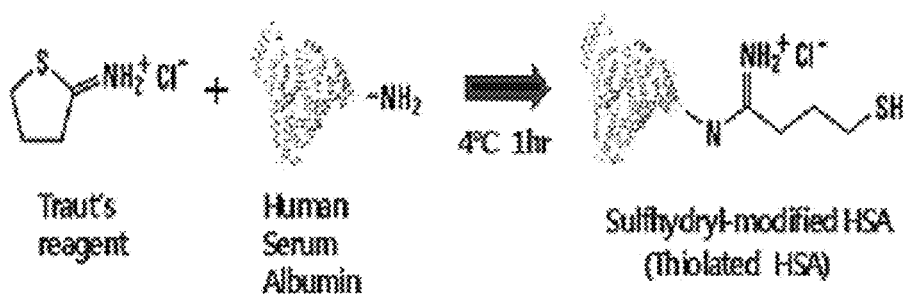
FIG. 1 is a schematic diagram of preparing a thiolated human serum albumin (T-HSA) by introducing —SH (thiol group) into human serum albumin (HSA) which containing amine group using Traut's reagent.

Hereinafter, this specification will be described in detail.

This specification provides siRNA carrier system, which is prepared by binding human serum albumin polymer to siRNA, especially, by a biodegradable covalent bond, for efficiently delivered siRNA in a living body.

The siRNA carrier system is prepared by binding human serum albumin to various forms of siRNAs. The binding may be acquired by a biodegradable covalent bond, and its structure can be expressed as follows.

A-B (A: human serum albumin, B: various forms of poly-siRNA)

where A denotes a human serum albumin, having a biodegradable reactor introduced thereinto. In detail, the human serum albumin A may efficiently form complexes with various forms of siRNAs in an aqueous solution to create nano-sized self-assemblies, thus to be selectively accumulated on a specific disease sites (e.g., angiogenesis-targeting EPR, cancer, rheumatism, inflammatory diseases, etc.).

The serum albumin as one of in vivo polymer materials has a superior biocompatibility. Also, the serum albumin as a very stable protein having 19-day half life in blood has high affinity with tumor (cancer) tissues so as to exhibit effective cancer accumulation ability. Hence, the serum albumin may be chemically bound to various kinds of chemical drugs with a low molecular weight, proteins, antibodies and the like so as to be used for enhancing in vivo stability of various drugs and delivering such drugs to target tumor tissues. For example, a research, in which doxorubicin (Drug Delivery 6 (1999) 1-7) or methotrexate (MTX: Anticancer Drugs 8 (1997) 835-844) is chemically bound to albumin to enhance tumor targeting and stability of drugs within blood, has been reported. In regard of use of the albumin as a drug delivery, a research, in which a large amount of albumin is selectively accumulated on tumor tissues when the albumin having a bonded fluorophore or marked isotope is injected into cancer-grafted small animals based on its high targeting to the cancer tissues and then imaged, has been reported (Cancer Research 46 (1986) 6387-6392). Accordingly, it can be known that such selective accumulation is derived by an enhanced permeability and retention (EPR) effect, which occurs in loose blood vessels near tumor tissues. Thus, the superiority of the albumin as the anticancer delivery has been introduced, but the albumin itself does not afford a binding (bonding) force as strong as being able to be used as siRNA carrier system having strong negative charges. Hence, a variation that the albumin-specific features are maintained with increasing the binding force is needed.

So, the present inventors have studied a method for stably binding human serum albumin with siRNA to prepare human serum albumin-siRNA carrier system capable of stably delivering the siRNA in a living body by virtue of an effective binding with the siRNA. Consequently, the inventors have found that when siRNA is bound to the human serum albumin by a biodegradable covalent bond, the siRNA and the human serum albumin can be stably bound to each other and effectively degradable in vivo, thus to be appropriate as siRNA carrier system. For reference, the inventors have presented a patent application and a paper for poly-siRNA having enhanced in vivo stability and gene expression effect of siRNA by introducing a thiol group into 5' terminal of siRNA to bind the siRNA by a disulfide bond to thus increase the size of siRNA (PCT/KR2010/001296, Journal of controlled release, 2010. 141 (3): 339-346). Also, possibility as siRNA carrier system has been confirmed by simultaneously introducing charge and covalent bond into polymers derived from a living body to make nanoparticles having an enhanced reactivity (Patent Application No. 2010-0089081).

Human serum albumin A and siRNA B of human serum albumin-siRNA carrier system according to this specification are bound to each other by a biodegradable covalent bond. Examples of the biodegradable covalent bond may include, but not limited to, disulfide bond, ester bond, anhydride bond, hydrazone bond, enzyme-specific peptide bond and the like. Such biodegradable covalent bond may be useful in view of being degradable under a specific physiologic environment. The biodegradable bond between siRNA and human serum albumin, which are biodegradable by various enzymes and acidities under a physiologic environment, may allow siRNA, which is lysed by a specific in vivo enzyme or the like, to inhibit expression of a target protein. For example, when a thiol group, as a reactor for the biodegradable covalent bond, is introduced into a terminal of siRNA and a terminal of a polymer, the siRNA and the polymer have a biodegradable bond called the disulfide bond. The disulfide bond is reduced by glutathione (GSH) within cytoplasm. When siRNA-human serum albumin carrier system having the disulfide bond is introduced in a living body, the bond is digested by glutathione existing in the living body such that the siRNA can be separated from the carrier system. Especially, in regard of the report that the concentration of glutathione increases in cancer cells, it can be noticed that the biodegradable bond, such as the disulfide bond, of human serum albumin-siRNA nano-sized carrier system, can be effectively biodegraded even in tumor tissues to effectively deliver siRNA to target tissues.

For the biodegradable covalent bond, a biodegradable reactor is introduced into the human serum albumin A, and also a reactor is introduced into one or both terminals of siRNA B for the biodegradable covalent bond with the human serum albumin A. The type of reactor introduced may depend on a targeting type of covalent bond.

In the above description, B denotes various forms of siRNAs each having a reactor. The siRNA may be monomer siRNA, poly-siRNA which bound with several siRNAs by a biodegradable bond, or polymerized siRNA. Preferably, the siRNA may be 15 to 30 nucleotide monomer siRNAs or polymerized siRNA, which is composed of 100 to 600 nucleotides as its polymers. The molecular weight of the siRNA may preferably be in the range of 10,000 to 1,000,000. The siRNA sequence may preferably use, but not to limited to, a base sequence for vascular endothelial growth factor (VEGF), Bcl2, EGFR, NF-kB and the like for the purpose of treatment (therapy). The following examples used siRNA base sequence for a red fluorescence protein (RFP) for checking a delivery efficacy of siRNA by fluorescence. The human serum albumin A and siRNA B may preferably be mixed approximately in a weight ratio of 10:1.

A method for preparing siRNA carrier system by binding human serum albumin A and siRNA B according to this specification may include:

(a) introducing a reactor for biodegradable covalent bond into the human serum albumin;

(b) introducing or activating a reactor into one or both terminals of various forms of siRNAs; and (c) stably binding the human serum albumin prepared at step (a) and the siRNAs prepared at step (b) by the biodegradable covalent bond to prepare nanoparticles.

The method may alternatively be configured to simultaneously perform those steps according to a binding mechanism. In one embodiment of this specification, a thiol group was introduced into the human serum albumin to prepare a thiolated human serum albumin (see FIG. 1). Also, the thiolated human serum albumin was then bound to polymerized poly-siRNAs each having a thiol group-introduced terminal. Accordingly, the human serum albumin and poly-siRNAs could form complexes by a disulfide bond derived by the introduced thiol group. Thus, the thiol group or a reactor other than the thiol group may be introduced into the human serum albumin and siRNA to form a complex by a covalent bond therebetween.

As aforesaid, the various forms of siRNAs having the reactors introduced thereinto and the reactor-introduced human serum albumin may efficiently form complexes in an aqueous solution to form nano-sized self-assemblies, which may also be accumulated on a specific disease sites (e.g., angiogenesis-targeting EPR, cancer, rheumatism, inflammatory diseases, etc.). Regarding of this, only the siRNA is difficult to be permeated into cells due to its sufficient negative charges, but the human serum albumin bound to the siRNA is a very stable protein, which has 19-day half life within blood and is tried to be used as a drug delivery system for improving in vivo stabilities of various drugs. Consequently, the siRNA and the human serum albumin can form nano-sized self-assemblies by virtue of the chemical modification of the human serum albumin. A drug bond level of siRNA and the like may be controlled according to a degree of the modification. When delivering siRNA using a carrier system according to this specification, the siRNA may allow an effective drug circulation in vivo and be utilized as a drug delivery system having a high accumulation ability with respect to tumor tissues.

The human serum albumin-siRNA carrier system fabricated by the method may be 10 to 2000 nm in size and form nanoparticles in a living body, thus to be effectively accumulated on tumor tissues by an EPR effect and appropriate for cancer treatment. In addition, for inflammatory diseases such as rheumatoid arthritis and the like, blood vessel may be extended by a secreted/induced inflammatory material, and blood pressure and permeability may be increased, such that an anti-inflammatory agent can be delivered into inflammatory cells present at a vascular wall. Hence, the siRNA carrier system according to this specification may also be suitable for treating the inflammatory diseases.

In the meantime, the siRNA carrier system may be used as a significant component of a pharmacological composition. Therefore, this specification provides a pharmacological composition consisting of an effective dose of human serum albumin-siRNA carrier system.

The pharmacological composition may further include one or more types of pharmacologically allowable carriers for administration, in addition to the human serum albumin-siRNA carrier system.

The pharmacological allowable carriers may be compatible with the significant component. As the pharmacological allowable carrier, saline solution, sterile water, ringer's solution, buffered saline water, dextrose solution, maltodextrin solution, glycerol, ethanol and a mixture of at least one thereof may be used, or if necessary, other typical excipient, such as antioxidant, buffer solution, bacteriostatic agent and the like, may be added. Also, diluent, dispersing agent, surfactant, binder and lubricant may additionally be added to be prepared into a formation for injection, such as aqueous solution, suspension, emulsion and the like.

The pharmacological composition may be prepared into various forms, such as powders, tablet, capsule, liquid medicine, injection, ointment, syrup and the like, and be provided by use of a unit-dosage or multi-dosage container, for example, a sealed ampule and bottle and the like.

The pharmacological composition may be allowed for oral or parenteral administration. Administrations of the pharmacological composition may be carried out by one of methods including, but not limited to, oral administration, intravenous administration, intramuscular administration, intraarterial administration, intramedulary administration, intradural administration, intracardiac administration, transcutaneous administration, subcutaneous administration, intraperitoneal administration, intestinal administration, sublingual administration or local administration. The pharmacological composition may be prepared into an appropriate formation by using well-known technologies for such clinical administrations. For example, upon an oral administration, the pharmacological composition may be mixed with an inactive diluent or edible carrier, sealed in a hard or soft gelatin capsule or pressed into tablets for administration. For the oral administration, the active compound may be mixed with a diluting agent to be used in form of ingestible tablet, buccal tablet, troche, capsule, elixirs, suspension, syrup, wafer and the like. Also, various formations for, for example, injection, parenteral administration and the like may be fabricated according to known techniques in the field of this specification or a commonly used technique.

The dosage of the composition may vary within a wide range according to weight, age, gender, health status, diet, administration time, administration manner, excretion rate, severity of disease and the like, all related to patients, and be decided by typical exports in the art the present disclosure belongs to.

Hereinafter, this specification will be described in detail with reference to several examples. The following examples are merely illustrative, and should not be construed as limiting the present disclosure.

Example 1

Thiol Group Introduction into Human Serum Albumin (T-HSA Preparation)

A large amount of human serum albumin is present in a living body without toxicity and efficiently accumulated on tumor tissues. However, it is impossible to be bound by itself to siRNA with strong negative charges. Therefore, thiol group was introduced into amine group of albumin by use of Traut's reagent as a cross-linker (here, SPDP cross-linker may be used instead of Traut's reagent). The introduction of the thiol group into the albumin using the Traut's reagent may be easily carried out in an aqueous solution, and the albumin containing the thiol group may efficiently have a disulfide bond with siRNA, which has thiol group at one or both terminals thereof. The disulfide bond may allow that the disulfide-bonded portion is specifically lysed by glutathione within cytoplasm to make siRNA released.

10 mg of human serum albumin (HSA, a molecular weight of 66.5 kDa) was dissolved in 10 ml of phosphate buffer, whose pH was 8.0, and reacted respectively with 0.2, 0.4, 2 and 4 mg of Traut's reagents (a molecular weight of 137.63 Da, ratios of the number of molecules to the albumin were 10, 20, 100 and 200 times) at 4° C. for an hour. Afterwards, the solution was dialyzed for 24 hours using dialyzer membranes having cut-off of 12,000 Da to remove the non-reacted Traut's reagent, followed by lyophilization, thereby preparing thiolated human serum albumin (T-HSA) (see FIG. 1).

Example 2

Figure 2:
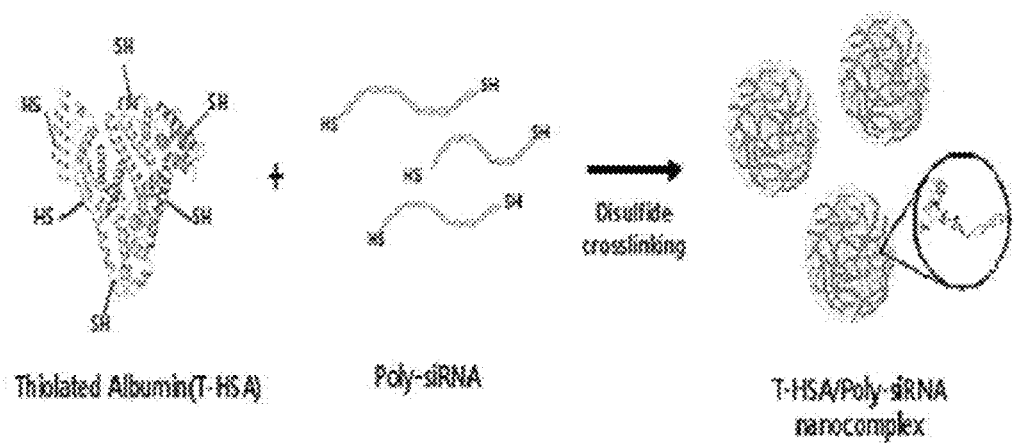
FIG. 2 is a schematic diagram of reacting poly-siRNA which containing —SH (thiol group) at both terminals thereof with the thiolated human serum albumin (T-HSA) to form complexes by a disulfide bond.

Binding of Polymerized Oligonucleotide Having Thiol Group and Human Serum Albumin Polymer Polymerized poly-siRNA whose stability and an amount of negative charges are increased by introducing thiol group into its terminal was bound to the T-HSA. The human serum albumin (T-HSA) and the siRNA formed complexes by the disulfide bond. 50 µg of poly-siRNA (50 mM sodium phosphate buffer, 5 mM EDTA, pH 8.0) and 500 μg of T-HSA were dissolved in 50 g of phosphate buffer (pH 8.0) and mixed to react with each other at 37° C. for 24 hours, thereby preparing a stabilized complexes (see FIG. 2).

Figure 3:
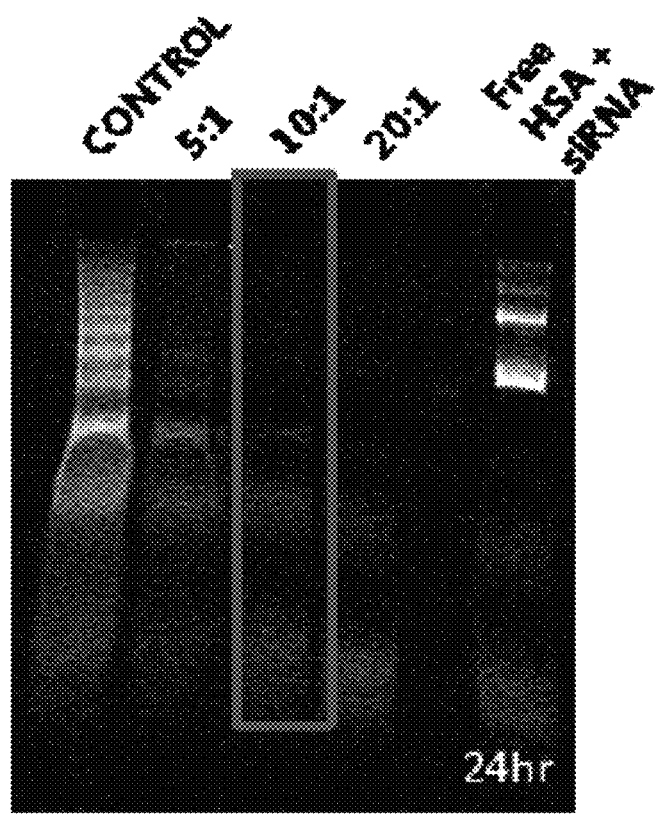
FIG. 3 is an electrophoretic image of the complexes of poly-siRNA and T-HSA prepared by the disulfide bond.

The complexes, which were prepared by mixing the poly-siRNA and the T-HSA were mixed in several weights and concentration ratios and reacted with each other at 37° C. for 24 hours, were electrophoresed at 150V for 35 minutes in 8% of polyacrylamide gel (see FIG. 3). Afterwards, the electrophoresed complexes were stained with Et—Br, thereby observing poly-siRNA, which remained without reaction upon forming the complexes, by use of a gel document system.

Accordingly, it was observed that when Traut's reagent was added at a molar ratio of 100 times to the T-HSA and the T-HSA was added at a weight ratio of 10 times to siRNA and reacted, the most effective complexes of the T-HSA and poly-siRNA were formed. Also, it was observed that any binding of poly-siRNA to pure human serum albumin without a reactor introduced was not happened. Therefore, it was understood that the disulfide bond was made upon formation of the complexes between poly-siRNA and T-HSA by virtue of the thiol group in addition to charges.

Example 3

Figure 4:
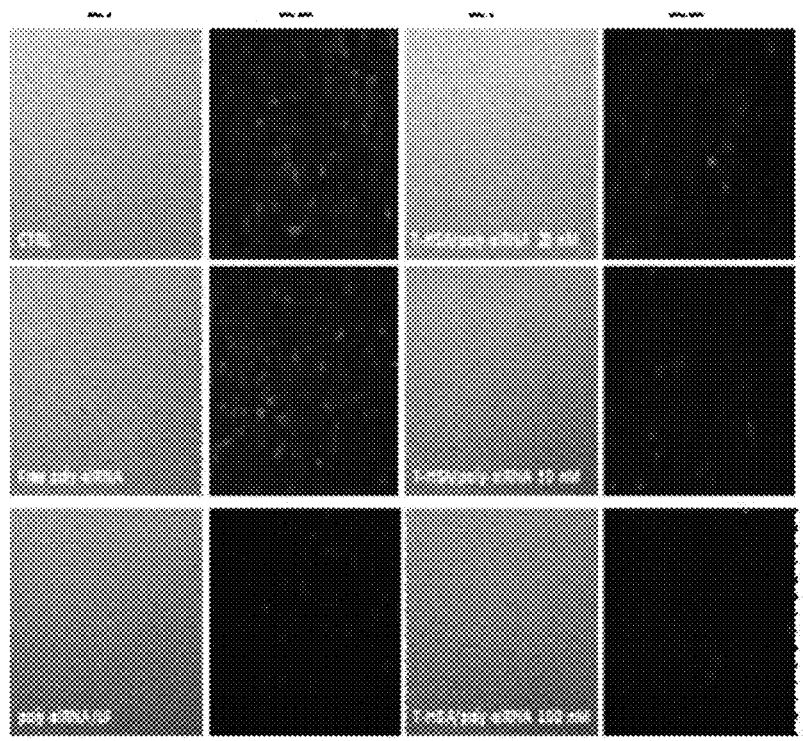
FIG. 4 shows inhibition effects of red fluorescence protein (RFP) gene expression by processing the RFP gene overexpressed cells with the T-HSA/poly-siRNA complexes for the RFP gene according to each concentration.

Verification of Gene Expression Inhibition by siRNA Delivery Using Complex of Thiol Group Introduced Human Serum Albumin (T-HAS) Polymer and Polymerized Oligonucleotide (Poly-siRNA) Through Cell Experiment The complex nanoparticles of poly-siRNA and T-HSA prepared according to Example 2 were processed in RFP-B16/F10 ($1.2*10^5$/dish) cells as melanoma cell lines, from which RFP was overexpressed, such that the concentration of the siRNA could be 20 nM, 50 nM and 100 nM. After 24 hours, the red fluorescent protein (RFP) expression inhibition efficacies of the processed nanoparticles were observed in fluorescent microscopic images. In this experiment, siRNA targeting the RFP as a fluorescent protein was used. For verification of gene expression inhibition effects at a cell level, the experiment was carried out by dividing into a non-processed group (control group), an only poly-siRNA-processed group without a carrier system (free poly-siRNA), a poly-siRNA/LF processed group, and a poly-siRNA/T-HAS administrated group (see FIG. 4). The LF of the poly-siRNA/LF indicates Lipofectamine™ 2000, a product of Invitrogen Inc. It was observed through this experiment that the poly-siRNA delivery by the T-HSA exhibited an efficient inhibition of the RFP gene expression.

Example 4

Figure 5:
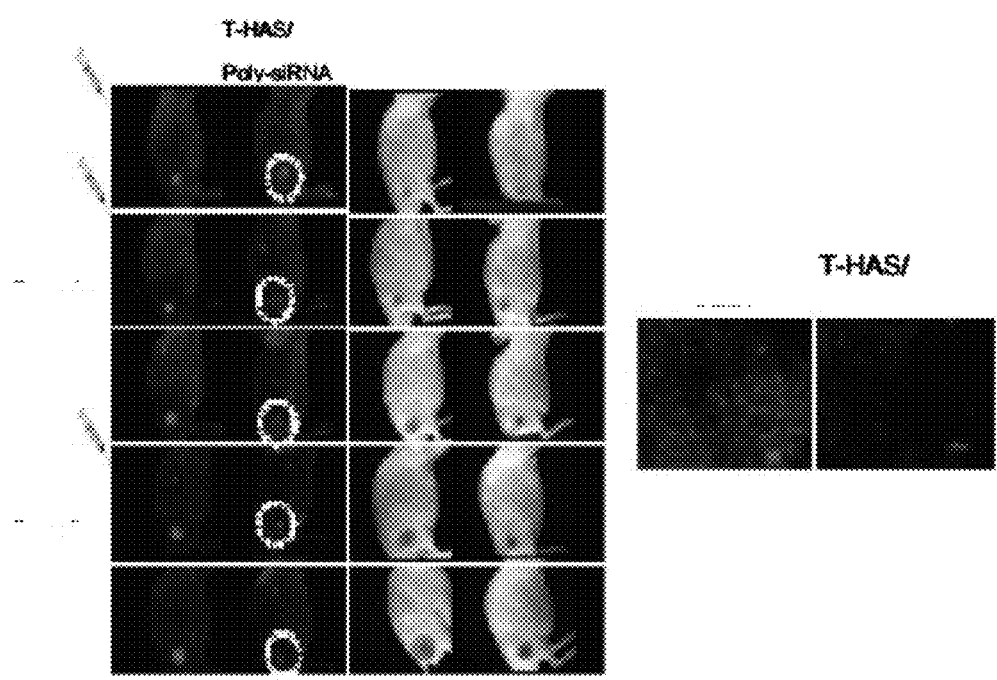
FIG. 5 shows gene expression inhibition effects in cancer tissues expressing the RFP after administrating the T-HSA/poly-siRNA complexes fabricated by a method of Example 2 into a mouse.

Verification of Gene Expression Inhibition Effect by siRNA Delivery Using Complex of T-HSA Polymer and Poly-siRNA Through Animal Experiment $1\times10^6$ RFP-B16/F10 melanoma cell lines were injected into a nude mouse from a portion below a waist of its back side, thereby preparing an animal cancer model. The T-HSA/poly-siRNA complexes, fabricated by the method of Example 2, was injected into a tail vein of the animal cancer model three times (day 0, day 1, day 3) from when RFP fluorescence was detected from the mouse through an optical imaging system, thereby observing the RFP expression inhibition effect from cancer tissues by virtue of the poly-siRNA delivered through blood vessels. It was observed that the RFP expression from the cancer tissues was remarkably reduced when injecting the T-HSA/poly-siRNA complexes (see FIG. 5). Also, an efficient reduction of RFP expression from the tissues of the T-HSA/poly-siRNA complexes-injected mouse was observed by way of avulsing cancer tissues from the mouse at the sixth day and comparing the RFP expression amounts from the cancer tissues through the fluorescent microscope.

Example 5

Examination of Tumor Volume Reduction by Deliver of Complex of T-HSA Polymer and Poly-siRNA Through Animal Experiment $1\times10^6$ PC-3 human prostatic carcinoma cell lines were injected into a nude mouse from a portion below a waist of its back side, thereby preparing an animal cancer model. Poly-siRNA for a vascular endothelial growth factor (VEGF), which directly affected tumor proliferation, was prepared and the T-HSA/poly-siRNA complexes were fabricated by the method of Example 2. The T-HSA/poly-siRNA complexes were injected into a tail vein of the animal cancer model at a two-day interval from when the tumor became about 50~100 $mm^3$ in volume, thereby measuring the reduction of the tumor volume by the VEGF poly-siRNA delivered via the vessels for three weeks. It was observed that upon the injection of the T-HSA/poly-siRNA complexes, the tumor proliferation within cancer tissues was remarkably inhibited by the VEGF inhibition.

As described above, the nano-sized human serum albumin-siRNA carrier system having a novel formation, fabricated by the biodegradable covalent bond, can form nanoparticles in an aqueous solution and stably deliver the siRNA into a target site in a living body, thereby enhancing therapy efficiency by the siRNA. Therefore, the human serum albumin-siRNA carrier system can usefully be applied to various cancers and disease models.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A human serum albumin-siRNA carrier system having a biodegradable covalent bond between human serum albumin A and siRNA B, the carrier system having the following structure,

A-B where A denotes human serum albumin polymer modified to have a biodegradable reactor, and B denotes polymerized siRNA (poly-siRNA) having a reactor introduced into one or both terminals thereof, and where the poly-siRNA consists of multiple monomer siRNAs connected to each other by a biodegradable bond.

2. The carrier system of claim 1, wherein the human serum albumin A and the poly-siRNA B have introduced reactors, respectively, for the biodegradable covalent bond therebetween.

3. The carrier system of claim 1, wherein the biodegradable covalent bond between the human serum albumin A and the poly-siRNA B is selected from disulfide bond, ester bond, anhydride bond, hydrazone bond and enzyme-specific peptide bond.

4. The carrier system of claim 1, wherein the poly-siRNA B is composed of 100 to 600 nucleotides.

5. The carrier system of claim 1, wherein the human serum albumin A and the poly-siRNA B are mixed in a weight ratio of 10:1.

6. The carrier system of claim 1, wherein the carrier system is 10 to 2000 nm in size.

7. The carrier system of claim 1, wherein the human serum albumin-siRNA carrier system is used for cancer treatment.

8. An anticancer composition consisting of an effective dose (amount) of human serum albumin-siRNA carrier system.

9. A method for fabricating siRNA carrier system comprising:
  (a) modifying human serum albumin polymer by introducing a reactor for biodegradable covalent bond into the human serum albumin polymer with positive charges;
  (b) introducing or activating a reactor into one or both terminals of polymerized siRNA (poly-siRNA); and
  (c) stably binding the human serum albumin polymer prepared at step (a) and the siRNA prepared at step (b) by the biodegradable covalent bond to prepare nanoparticles, and wherein the poly-siRNA consists of multiple monomer siRNAs connected to each other by a biodegradable bond.

\* \* \* \* \*